(12) United States Patent
Tanzer et al.

(10) Patent No.: US 6,429,350 B1
(45) Date of Patent: Aug. 6, 2002

(54) ABSORBENT ARTICLE HAVING SUPERABSORBENT POCKETS IN A NON-ABSORBENT CARRIER LAYER

(75) Inventors: Richard Warren Tanzer, Neenah; Bruce Reed Shafer, Green bay, both of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/385,514

(22) Filed: Aug. 27, 1999

(51) Int. Cl.$^7$ ............................................. A61F 13/15
(52) U.S. Cl. ........................................ 604/368; 604/367
(58) Field of Search ........................ 604/385.16, 364, 604/367, 368, 378

(56) References Cited

U.S. PATENT DOCUMENTS

| | | | |
|---|---|---|---|
| 3,881,489 A | * 5/1975 | Hartwell | 128/287 |
| 3,901,236 A | 8/1975 | Assarsson et al. | 128/284 |
| 4,055,180 A | * 10/1977 | Karami | 128/287 |
| 4,062,817 A | 12/1977 | Westerman | 260/17.45 G |
| 4,076,663 A | 2/1978 | Masuda et al. | 260/17.4 GC |
| 4,259,387 A | 3/1981 | Mesek | 428/167 |
| 4,286,082 A | 8/1981 | Tsubakimoto et al. | 526/240 |
| 4,340,706 A | 7/1982 | Obayashi et al. | 526/207 |
| 4,685,914 A | 8/1987 | Holtman | |
| 4,699,619 A | 10/1987 | Bernardin | 604/378 |
| 4,798,603 A | 1/1989 | Meyer et al. | 604/378 |
| 4,834,735 A | 5/1989 | Alemany et al. | 604/368 |
| 4,847,134 A | 7/1989 | Fakrenkrug et al. | 428/138 |
| 4,892,535 A | 1/1990 | Björnberg et al. | |
| 5,147,343 A | 9/1992 | Kellenberger | 604/368 |
| 5,149,335 A | 9/1992 | Kellenberger et al. | 604/372 |
| 5,272,236 A | 12/1993 | Lai et al. | 526/348.5 |
| 5,322,728 A | 6/1994 | Davey et al. | 428/296 |
| 5,364,382 A | 11/1994 | Latimer et al. | 604/378 |
| 5,366,452 A | 11/1994 | Widlund et al. | 604/385.2 |

(List continued on next page.)

FOREIGN PATENT DOCUMENTS

| | | | |
|---|---|---|---|
| EP | 875 224 | 11/1998 | |
| WO | 96/16624 | 6/1996 | ........... A61F/13/15 |
| WO | 98/37846 | 9/1998 | |

*Primary Examiner*—John G. Weiss
*Assistant Examiner*—Michael Bogart
(74) *Attorney, Agent, or Firm*—Pauley Petersen Kinne & Erickson (57) ABSTRACT

An absorbent article having relatively light weight and less bulk includes a liquid permeable top layer, an inner surge layer, and a substantially liquid-impermeable outer cover. A plurality of pockets are formed in at least one of the surge layer and the outer cover material. The pockets contain a superabsorbent material. The surge layer or outer cover material containing the pockets functions as an absorbent layer, thereby eliminating the need for a separate (often bulky) absorbent layer between the surge layer and the outer cover.

27 Claims, 4 Drawing Sheets

U.S. PATENT DOCUMENTS

| | | | |
|---|---|---|---|
| 5,376,198 A | | 12/1994 | Fakrenkrug et al. ......... 156/164 |
| 5,389,095 A | | 2/1995 | Suzuki et al. ............ 604/385.2 |
| 5,411,497 A | | 5/1995 | Tanzer et al. ............... 604/368 |
| 5,422,169 A | * | 6/1995 | Roe .......................... 428/212 |
| 5,425,725 A | | 6/1995 | Tanzer et al. ............... 604/368 |
| 5,433,715 A | | 7/1995 | Tanzer et al. ............... 604/368 |
| 5,451,219 A | | 9/1995 | Suzuki et al. ............ 604/385.2 |
| 5,494,622 A | | 2/1996 | Heath et al. ................ 264/40.1 |
| 5,509,915 A | | 4/1996 | Hanson et al. .............. 604/378 |
| 5,520,673 A | | 5/1996 | Yarbrough et al. ......... 604/378 |
| 5,560,878 A | | 10/1996 | Dragoo et al. .............. 264/115 |
| 5,562,645 A | * | 10/1996 | Tanzer et al. ............... 604/367 |
| 5,571,619 A | | 11/1996 | McAlpin et al. ............ 428/364 |
| 5,593,399 A | | 1/1997 | Tanzer et al. ............... 604/368 |
| 5,601,542 A | | 2/1997 | Melius et al. ............... 604/368 |
| 5,643,238 A | * | 7/1997 | Baker ......................... 604/368 |
| 5,643,239 A | * | 7/1997 | Bodford et al. ............. 604/370 |
| 5,645,542 A | | 7/1997 | Anjur et al. ................ 604/368 |
| 5,662,634 A | | 9/1997 | Yamamoto et al. ......... 604/378 |
| 5,683,374 A | | 11/1997 | Yamamoto et al. ...... 604/385.2 |
| 5,788,684 A | * | 8/1998 | Abuto et al. ................ 604/368 |
| 5,824,004 A | | 10/1998 | Osborn, III et al. ..... 604/385.2 |
| 5,865,824 A | | 2/1999 | Chen et al. |
| 5,883,028 A | | 3/1999 | Morman et al. ............ 442/394 |
| 5,904,675 A | | 5/1999 | Laux et al. ............. 604/385.2 |
| 5,928,209 A | * | 7/1999 | Bodford et al. ............. 604/370 |
| 5,938,650 A | | 8/1999 | Baer et al. |
| 5,941,864 A | * | 8/1999 | Roe .......................... 604/378 |
| 6,290,686 B1 | * | 9/2001 | Tanzer .................. 604/385.01 |

* cited by examiner

ABSORBENT ARTICLE HAVING SUPERABSORBENT POCKETS IN A NON-ABSORBENT CARRIER LAYER

FIELD OF THE INVENTION

This invention relates to an absorbent article in which superabsorbent material is contained in pockets of another, non-absorbent layer. The invention eliminates the need for a separate absorbent layer, and reduces the total number of layers required in the article.

BACKGROUND OF THE INVENTION

Absorbent composites suitable for use in disposable absorbent garments such as diapers, adult incontinent products, and the like, are known. Such absorbent composites are described, for example, in U.S. Pat. No. 4,699,619 issued Oct. 13, 1987 to Bernardin, U.S. Pat. No. 4,798,603 issued Jan. 17, 1989 to Meyer et al., U.S. Pat. No. 4,834,735 issued May 30, 1989 to Alemany et al., U.S. Pat. No. 5,147,343 issued Sep. 15, 1992 to Kellenberger, and U.S. Pat. No. 5,149,335 issued Sep. 22, 1992, to Kellenberger et al.

Generally, such absorbent composites comprise a matrix for containing a high-absorbency material in another absorbent material. Suitable matrices for containing the high-absorbency material include absorbent fibrous matrixes, such as those formed from air-laid cellulosic fibers or a coform material comprising cellulosic fibers and meltblown polyolefin fibers. A wide variety of high absorbency materials (also known as superabsorbent materials) are known to those skilled in the art. See, for example, U.S. Pat. No. 4,076,663 issued Feb. 28, 1978 to Masuda et al, U.S. Pat. No. 4,286,082 issued Aug. 25, 1981 to Tsubakimoto et al., U.S. Pat. No. 4,062,817 issued Dec. 13, 1977 to Westerman, and U.S. Pat. No. 4,340,706 issued Jul. 20, 1982 to Obayashi et al.

Many known absorbent composites comprising a high-absorbency material employ the high-absorbency material in relatively low concentrations. That is, many of the absorbent composites comprise air-laid cellulosic fibers and less than about 20 weight percent of high-absorbency material. This is due to several factors.

Many high-absorbency materials are unable to absorb a liquid at the rate at which the liquid is applied to the absorbent composites during use. Accordingly, a relatively high concentration of fibrous material is desirable to temporarily hold the liquid until the high-absorbency material can absorb it. Further, the fibers serve to separate the particles of high-absorbency material so that gel-blocking does not occur. Gel-blocking refers to the situation wherein particles of high-absorbency material deform during swelling and block the interstitial spaces between the particles, or between the particles and fibers, thus preventing the flow of liquid through the interstitial spaces.

The presence of a relatively low concentration of high-absorbency material and a relatively greater concentration of fibrous materials has resulted in the production of absorbent composites which tend to be relatively thick. In some instances, the use of a relatively thick absorbent composite in a disposable absorbent garment is acceptable. However, in recent years it has become increasingly desirable to produce absorbent composites which are thin compared to the more traditional absorbent composites but which still possess the same absorbent capacity. The desire to produce relatively thin absorbent composites has resulted in the desire to incorporate ever-increasing amounts of high-absorbency material into the absorbent composites. This is because the absorbent capacity of such high-absorbency materials is generally many times greater than the absorbent capacity of fibrous materials. For example, a fibrous matrix of wood pulp fluff can absorb about 7–9 grams of a liquid, (such as 0.9 weight percent saline) per gram of wood pulp fluff, while the high-absorbency materials can absorb at least about 15, preferably at least about 20, and often at least about 25 grams of liquid, such as 0.9 weight percent saline, per gram of the high-absorbency material.

U.S. Pat. No. 5,601,542, issued to Melius et al., discloses an absorbent article in which superabsorbent material is contained in layers of discrete pouches. The pouches are adjacent one another, and are formed in one or more substrate layers. The patent illustrates a diaper which includes a substantially liquid impermeable outer cover, a liquid permeable body-side liner, and an absorbent composite between the outer cover and body-side liner. A surge management layer, positioned adjacent to the body-side liner in the crotch region of the latter, regulates the flow of liquid surging into the absorbent composite. The surge management. layer may be above (on the outside of) the body-side liner, or may be between the body-side liner and the absorbent composite.

There is a need or desire in the industry to provide diapers and other absorbent articles having fewer layers, lighter construction, and lower production costs, without losing any of the functions provided by the conventional layers.

SUMMARY OF THE INVENTION

The present invention is an absorbent article, such as a diaper, in which the functions of plural layers are combined into a single layer, thereby reducing the total number of layers without yielding any functions. Specifically, the present invention is directed to an absorbent article, such as a diaper, in which the absorbent function is integrated into either the surge material or the outer cover material, thus eliminating the need for a separate central absorbent composite. The objective of the invention is accomplished by forming a plurality of small pockets in the surge material and/or the outer cover material. A superabsorbent material is added to the pockets, causing the surge layer and/or the outer cover to perform an absorbent function.

More specifically, the present invention is directed to an absorbent article including a liquid-permeable body-side liner, a surge layer adjacent to the body-side liner, and a substantially liquid-impermeable outer cover adjacent to the surge layer. At least one of the surge layer and the outer cover includes a plurality of pockets, and a quantity of superabsorbent material within the pockets. Put another way, the pockets containing the superabsorbent can be in the surge layer, in the outer cover, or in both the surge layer and the outer cover material, thus eliminating the need for a separate absorbent composite layer between the surge layer and the outer cover material.

With the foregoing in mind, it is a feature and advantage of the invention to provide an absorbent article having three essential layers, namely a body-side liner, a surge layer, and an outer cover, wherein at least one of the surge layer and outer cover contains a superabsorbent material.

It is also a feature and advantage of the invention to provide an absorbent article having lower cost, simpler construction and lighter weight than conventional absorbent articles.

It is also a feature and advantage of the invention to provide an absorbent article having less bulk than conventional absorbent articles.

It is also a feature and advantage of the invention to provide a highly water vapor breathable absorbent garment, promoting skin wellness.

The foregoing and other features and advantages of the invention will become further apparent from the following detailed description of the presently preferred embodiments. This detailed description is exemplary, and should be construed as illustrating rather than limiting the invention.

DETAILED DESCRIPTION OF THE PRESENTLY PREFERRED EMBODIMENTS

The present invention is an absorbent article in which the functions of plural layers are combined into a single layer, thus eliminating the need for a separate absorbent core layer. The absorbent article includes a liquid-permeable body-side liner, a surge material adjacent the body-side liner, and a substantially liquid-impermeable outer cover adjacent the surge layer. Pockets are formed in at least one of the surge layer and outer cover, and a superabsorbent material is present in the pockets.

Figure 1:
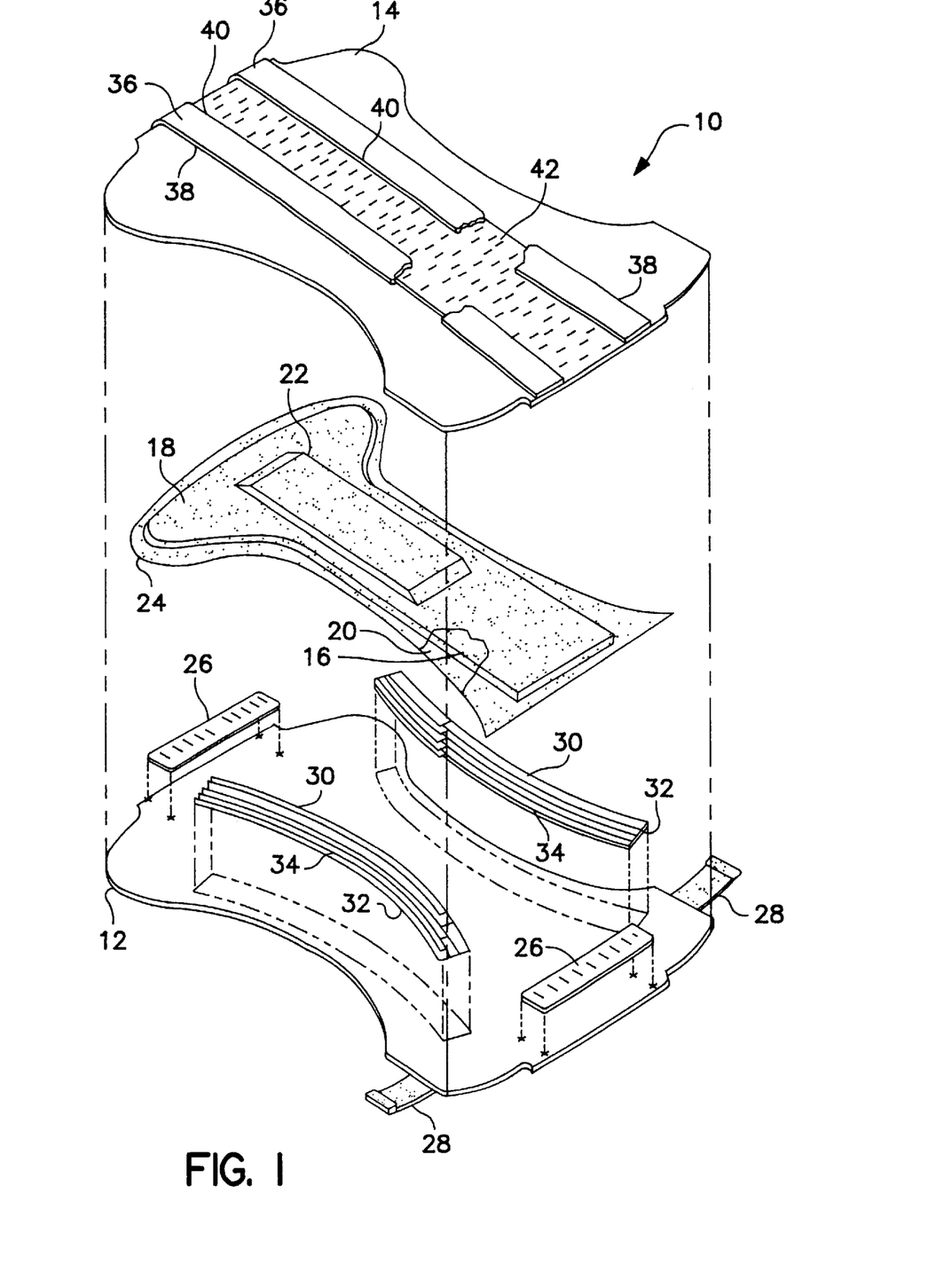
FIG. 1 is an exploded perspective view of a prior art absorbent article, in this case a diaper.

The features and advantages of the invention will be described with reference to a prior art disposable diaper. FIG. I illustrates an exploded perspective view of a disposable diaper of the prior art. Referring to FIG. 1, disposable diaper 10 includes an outer cover 12, a body-side liner 14, and an absorbent composite 16 located between the body-side liner 14 and the outer cover 12. The absorbent composite 16 comprises an air-laid mixture of wood pulp fibers and superabsorbent material. The absorbent composite is surrounded by a two-piece wrap sheet comprising upper wrap sheet layer 18 and lower wrap sheet layer 20. The absorbent composite 16 has a profiled thickness to define an area 22 of increased basis weight. The two-piece wrap sheet extends beyond the edges of the absorbent composite 16 to define perimeter 24 which can be sealed to prevent superabsorbent material from migrating out of the diaper.

Attached to outer cover 12 are waist elastics 26, fastening tapes 28 and leg elastics 30. The leg elastics 30 comprise a carrier sheet 32 and individual elastic strands 34.

The body-side liner 14 includes containment flaps 36 having proximal edges 38 and distal edges 40. A surge management layer 42 is located between the proximal edges 38 of the containment flaps 36.

The exact construction method and materials of the diaper illustrated in FIG. 1 are set forth in greater detail in commonly assigned U.S. Pat. No. 5,509,915, issued Apr. 23, 1996 in the name of Hanson et al., incorporated herein by reference. Possible modifications to the diaper illustrated in FIG. 1 are set forth in commonly assigned U.S. Pat. No. 5,509,915 referenced above and in commonly assigned U.S. Pat. No. 5,364,382, issued Nov. 15, 1994 to Latimer et al. Such possible modifications include positioning the surge management layer 42 between the body-side liner 14 and the absorbent composite 16 and reducing the length of the surge management layer to extend the length of the absorbent composite or massing (reduce length and increase basis weight) the surge management layer in the area of the diaper where liquid waste initially accumulates (target zone).

Figure 2:
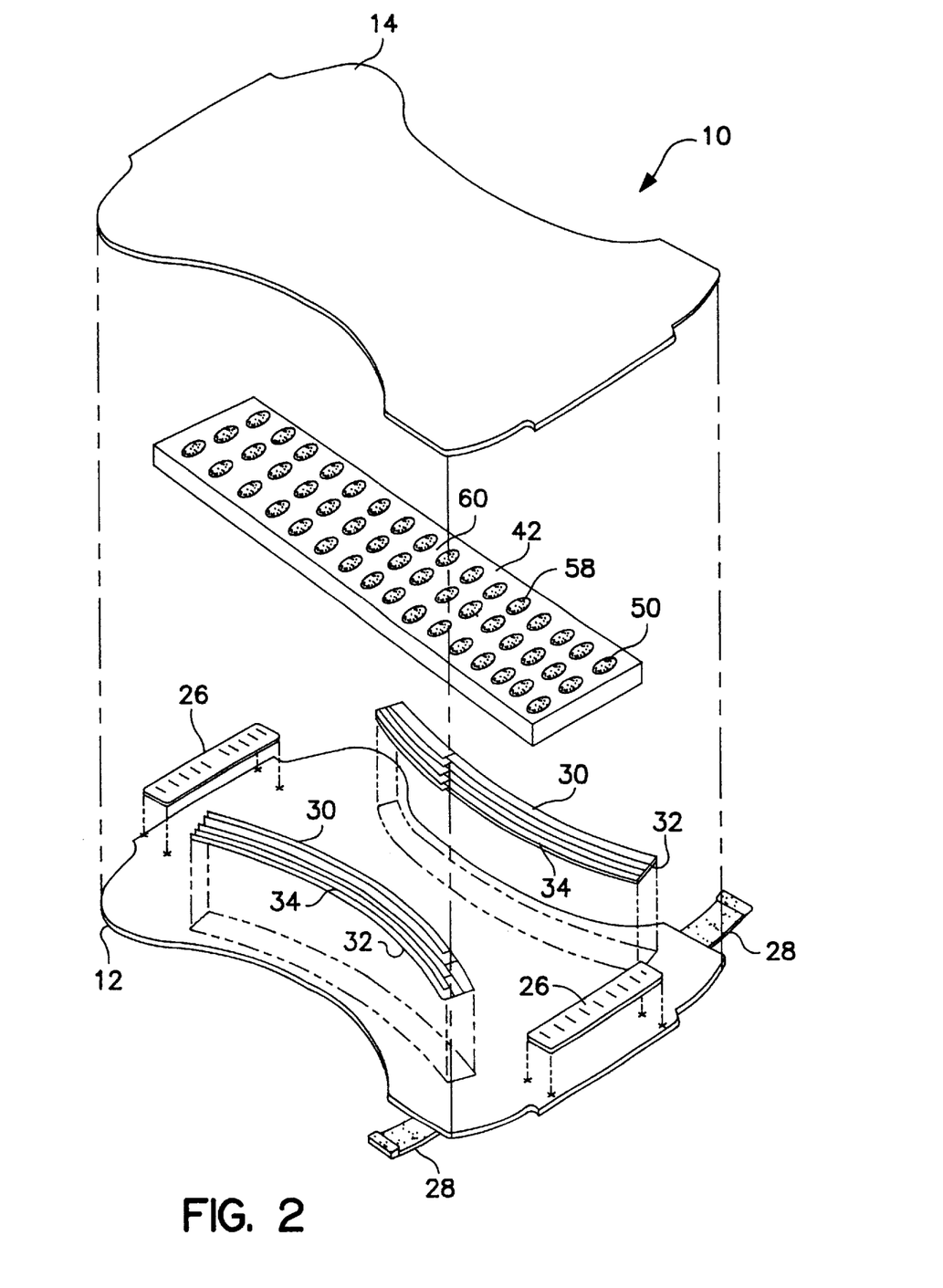
FIG. 2 is an exploded perspective view of a diaper according to the invention.

FIG. 2 illustrates one embodiment of a disposable diaper of the invention. In the diaper of FIG. 2, the absorbent composite 18 has been eliminated and the surge layer 42 has been placed between the liquid-permeable body-side liner 14 and the substantially liquid-impermeable outer cover 12. In accordance with the invention, a plurality of pockets 50 are formed in the surge layer 42. Pockets 50 each contain a quantity of superabsorbent material 58, thereby enabling the surge layer 42 to perform the dual functions of surge and absorbency. Surge layer 42 has an operable level of density and basis weight to quickly collect and temporarily hold liquid surges, to transport the liquid from its initial entrance point and to substantially completely release the liquid to pockets 50 and superabsorbent 58. This configuration can help prevent the liquid from pooling and collecting on the portion of the absorbent garment positioned against the wearer's skin, thereby reducing the feeling of wetness by the wearer.

The pockets 50 are spaced apart by distances 60. The spacings 60 between the pockets may be at least about 0.05 inch (1.3 mm), alternatively at least about 0.10 inch (2.5 mm), suitably at least about 0.15 inch (3.8 mm). Moreover, the spacings 60 are suitably not more than about 1.5 inch (38 mm), alternatively not more than about 1.0 inch (25 mm), alternatively not more than about 0.5 inch (13 mm).

The depths of pockets 50 may be at least about 0.1 inch (2.5 mm), preferably about 0.15–0.50 inch (3.8–13 mm), more preferably about 0.20–0.30 inch (5.1–7.6 mm). The pockets may have a circular or elliptical configuration, with diameters ranging from about 0.20–1.0 inch (5.1–25 mm), preferably about 0.25–0.75 inch (6.4–19.1 mm), more preferably about 0.40–0.60 inch (10.2–15.2 mm).

As explained further below, with respect to FIG. 3, pockets 50 may be variously configured with respect to the non-absorbent materials. For example, pockets 50 containing superabsorbent may exist between the surge management layer 42 and outer cover 12, or between two surge management layers.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations of Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrilegrafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbents may be particulate or fibrous, and are preferably particulate. Superabsorbents are generally available in particle sizes ranging from about 20 to about 1000 microns. Examples of commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® 880 available from Stockhausen, located in Sweden. FAVOR® 880 is presently preferred because of its high gel strength. An example of a fibrous superabsorbent is OASIS® 101, available from Technical Absorbents, located in Grimsby, United Kingdom.

Depending on the size of pockets 50 and density of the superabsorbent, each pocket 50 may contain about 25–500 mg of superabsorbent, preferably about 50–300 mg, more preferably about 100–200 mg. The number and size of pockets 50 may be such that surge layer 42 contains about 1–100 grams of total superabsorbent, preferably about 3–50 grams, more preferably about 5–15 grams. Of course, the total amount of superabsorbent 58 may vary depending on the size and intended use of the absorbent article. Furthermore, the superabsorbent 58 may be present in pockets formed in more than one non-absorbent layer of the diaper, as explained below.

In addition to the superabsorbent material, each pocket 50 may contain, if desired, a fibrous absorbent material such as pulp fibers, a filler material, an odor absorbent material, a fragrant material, or another suitable material. When combinations of materials are employed, the superabsorbent should constitute at least 30% of the total material in pockets 50, preferably at least 50%, more preferably at least 70%, most preferably at least 90%. Additionally, some of the pockets, preferably fewer than 50%, may contain no superabsorbent. The pockets without superabsorbent may contain odor absorbent materials, fragrances, lotions, emollients, antimicrobials and the like.

Pockets 50 will expand toward each other when the superabsorbent 58 becomes wet. Preferably, pockets 50 are shaped so that they may touch each other during expansion, without closing all of the space between them. When viewed from above, as in FIG. 2, pockets 50 preferably have a circular, oval or elliptical shape. Pockets having these shapes are also less likely to rupture due to stresses caused by swelling or stretching of the superabsorbent, and other forces experienced during product manufacture and use. Square and rectangular shapes are less preferred, because these shapes would permit substantially continuous contact along the edges of adjacent pockets 50. Also, pockets having these shapes are more easily ruptured.

Alternatively, the pockets 50 containing the superabsorbent 58 may be formed in another otherwise non-absorbent layer in the diaper. The term "non-absorbent" refers to any material which absorbs not more than about 5 times its weight in an aqueous solution containing 0.9% by weight sodium chloride. INDA Standard Test Method IST 10.1 (95), "Standard Test Method for Absorbency Time, Absorbency Capacity, and Wicking Time," published by INDA, Association of the Nonwoven Fabrics Industry, Cary, N.C., provides the basis for a suitable test method to measure absorbency. The "Absorptive Capacity Test (for small specimens)" may be used to determine the absorbency of a material for the purpose of the subject invention with the following two modifications: (i) IST 10.1 (95) specifies that water is to be used; substitute a 0.9% aqueous solution, (ii) IST 10.1 (95) specifies that a 5 gram sample is used. If necessary, a smaller sample, obtained from an absorbent product may be used instead.

Figure 3:
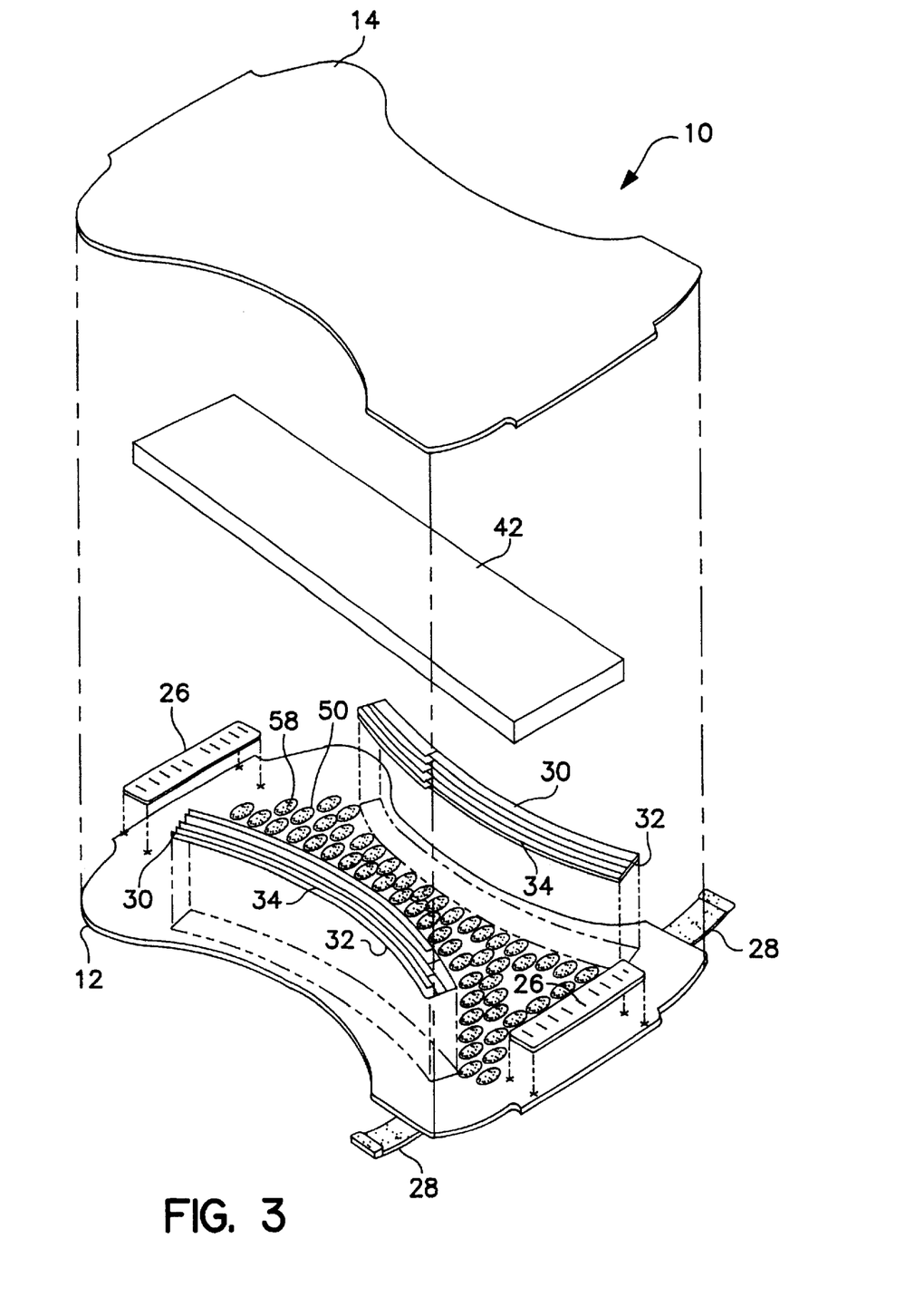
FIG. 3 is an exploded perspective view of another embodiment of a diaper according to the invention.

FIG. 3 illustrates a second embodiment of the invention, in which pockets 50 containing superabsorbent 58 are formed and located in the substantially liquid impervious outer cover material 12. In the embodiment shown, the pockets 50 are located beneath the surge layer 42, are between the two leg elastics 30, and are between the two waist elastics 26. One feature of this second embodiment, versus the first embodiment described above, is that the formation of pockets in the outer cover causes the outer surface of the outer cover material to have a dimpled, more textured feeling. The second embodiment also places the superabsorbent material as far as possible from the wearer's skin, thereby reducing skin irritation following liquid surges into the absorbent article.

The body-side liner 14, surge layer 42 and outer cover 12 are constructed of conventional non-absorbent materials. By "non-absorbent" it is meant that these materials, excluding the pockets filled with superabsorbent, have an absorptive capacity not exceeding 5 grams of 0.9% aqueous saline solution per gram of material, using the absorption test described above. Both the surge layer 42 and body-side liner 14 are constructed from highly liquid pervious materials. These layers function to transfer liquid from the wearer to the interior of absorbent article 10, ultimately to the superabsorbent 58 in pockets 50. Suitable liquid pervious materials include porous woven materials, porous nonwoven materials, films with apertures, open-celled foams, and batting. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof U.S. Pat. No. 5,904,675, issued May 18, 1999 to Laux et al. and incorporated by reference, provides further examples of suitable surge materials. Either layer may also be an apertured plastic film. Suitable batting includes certain air formed thermomechanical and chemithermomechanical wood pulps. The various layers of article 10 have dimensions which vary depending on the size and shape of the wearer.

The outer cover material 12 should be breathable to water vapor. Generally the outer cover 12 will have an MVTR of at least about 300 grams/m$^2$-24 hours using the test procedure described below, preferably at least about 1000 grams/m$^2$-24 hours, more preferably at least about 3000 grams/m$^2$-24 hours using the test procedure described below. Outer cover 12 shown in FIGS. 1–3 may include two layers, joined by thermal or ultrasonic bonding, or an adhesive. One of the layers can be a nonwoven filament web. The other layer can be a breathable film. Outer cover 12 can be positioned with the nonwoven web facing outward, and with the breathable film facing inward toward the surge layer 42.

Nonwoven filament webs can be used in the body-side liner 14, surge layer 42, and/or outer cover 12. Each nonwoven filament web may be a spunbond web, a meltblown web, a bonded carded web, an air-laid web, or any other filament-type nonwoven web which does not appreciably absorb aqueous fluid.

Preferably, each nonwoven web is made from one or more thermoplastic polymers. Suitable polymers include, without limitation, polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain, polyamides, and polyesters. Other suitable polymers include without limitation elastomers, for example polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly (ethylene-butylene)/polystyrene, poly (styrene/ethylene-butylene/styrene), and the like. Metallocene-catalyzed polyolefins are also useful, including those described in U.S. Pat. Nos. 5,571,619; 5,322,728; and 5,272,236, the disclosures of which are incorporated herein by reference.

Polymers made using metallocene catalysts have a very narrow molecular weight range. Polydispersity numbers (Mw/Mn) of below 4 and even below 2 are possible for metallocene-produced polymers. These polymers also have a controlled short chain branching distribution compared to otherwise similar Ziegler-Natta produced type polymers. It is also possible using a metallocene catalyst system to control the tacticity of the polymer quite closely.

Each nonwoven web is preferably made of polyethylene, polypropylene, or a semi-crystalline propylene-ethylene copolymer. In the outer cover 12, the web can be laminated to the breathable film using patterned thermal calender bonding, ultrasonic bonding, adhesive bonding, or the like. Preferably, the bonded regions will cover less than about 25%, more preferably less than about 20% of the interface between web 35 and film 37, so that the bonding does not impede breathability of the laminate 16.

The breathable film in the outer cover 12 can be formed from one or more of the same polymers as the nonwoven webs. In one embodiment, the breathable film is a microporous film which can be formed using a variety of known technologies. Preferably, the breathable film is formed from a known technique of mixing a polymer with about 50–75% particulate filler, such as calcium carbonate. A film is formed from the mixture, and the film is stretch-thinned to impart microporosity and breathability.

Figure 4:
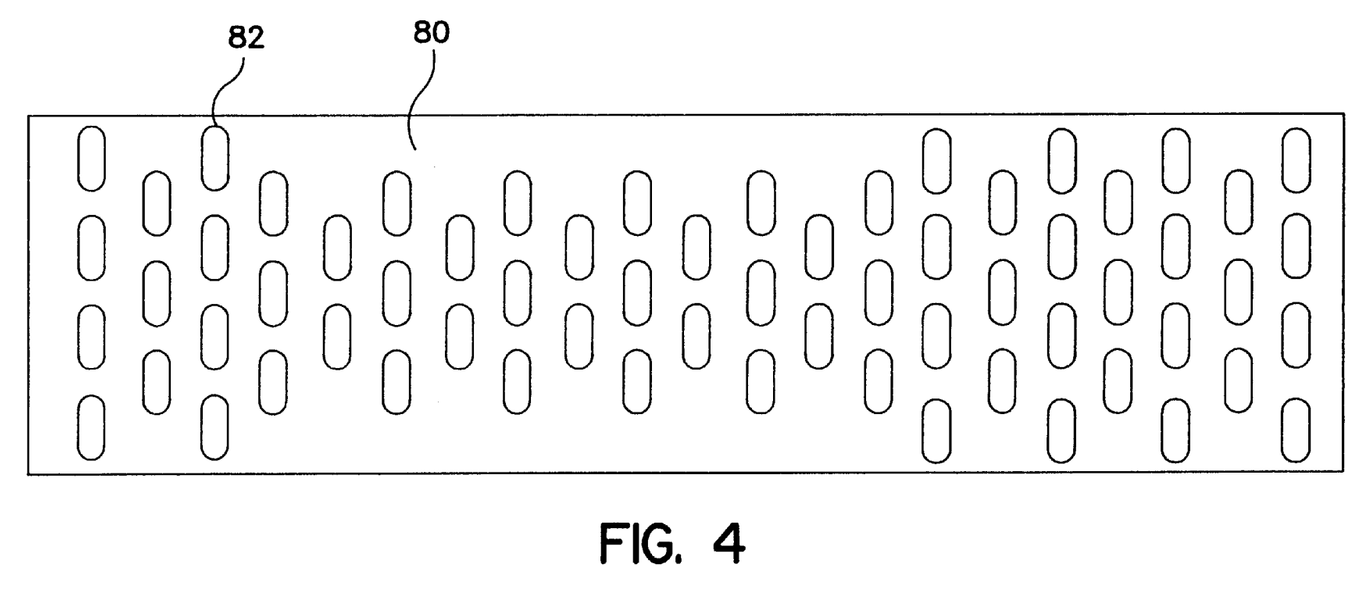
FIG. 4 illustrates one embodiment of a template for forming pockets in a layer of material.

FIG. 4 illustrates one embodiment of a template that can be used to form the pockets 50 in the surge layer 42 or the outer cover 12. Template 80 can have holes 82 slightly larger than the pockets to be formed. A non-absorbent layer material, for example a spunbond web, or a neck-stretched spunbond web, can be placed over the template 80. Then, a vacuum can be pulled through the openings 82 using, for instance, a vacuum box (not shown) that can be mounted beneath the template. The vacuum pulls the layer material into the holes 82, causing formation of the pockets.

At that point, the pockets 50 can be filled with superabsorbent 58, or a blend of superabsorbent 58 with another material. An adhesive can then be sprayed over the pocketed layer material, for instance, a hot melt adhesive, or any suitable adhesive known in the art for bonding layers of an absorbent article together. Then, the other layers of the absorbent article can be combined with the pocketed layer material and bonded together using an adhesive as described above, or using a variety of known ultrasonic and/or thermal bonding techniques. U.S. Pat. No. 5,494,622, issued Feb. 27, 1996 to Heath et al., discloses some methods of binding the layers of an absorbent article.

Small amounts of absorbent material may be present in the nonabsorbent material layer outside of the pockets. This is consistent with the invention, provided that the non-absorbent material layer has an absorptive capacity not exceeding 5 grams of 0.9% aqueous saline solution per gram of the non-absorbent layer excluding the pockets. Desirably the superabsorbent material in the pockets provides at least about 75% of the total absorptive capacity of the article, preferably at least about 90% of the total absorptive capacity of the article.

The resulting absorbent article eliminates at least one layer by combining the absorbent function with another, typically non-absorbent layer. As explained above, the pockets 50 containing superabsorbent 58 can be formed in a surge layer or an outer cover layer. In another embodiment, pockets 50 containing superabsorbent 58 may be formed in a plurality of non-absorbent layers, for instance, a surge layer and an outer cover layer. The absorbent article may be a diaper as described above, another personal care absorbent article, or a medical absorbent article. The term "personal care absorbent article" includes without limitation diapers, training pants, swim wear, absorbent underpants, baby wipes, adult incontinence products, and feminine hygiene products. The term "medical absorbent product" includes without limitation absorbent garments, underpads, bandages, absorbent drapes, and medical wipes.

Regardless of which layer the pockets 50 are formed in, the carrier layer material must have a suitable basis weight, i.e., not so light that it cannot effectively carry the superabsorbent 58 and not so heavy that the pockets 50 cannot be formed. For instance, the carrier material may have a basis weight of about 0.2–10 osy (6.8–34 gsm), suitably about 0.5–5 osy (17–170 gsm), desirably about 1–4 osy (34–136 gsm). When the carrier material contains multiple layers, as in the case of an outer cover, these basis weights are preferred for the combined (sum total) of layers.

Test Procedure For Measuring Moisture Vapor Transmission Rate (MVTR)

A measure of the breathability of a fabric is the moisture vapor transmission rate (MVTR), which for the sample materials is calculated essentially in accordance with ASTM Standard E96–80 with minor variations in test procedure as set forth below. Circular samples measuring three inches in diameter are cut from each of the test materials, and tested along with a control which is a piece of CELGARD® 2500 sheet from Celanese Separation Products of Charlotte, N.C. CELGARD® 2500 sheet is a microporous polypropylene sheet. Three samples are prepared for each material. The test dish is a number 60–1 Vapometer pan distributed by Thwing-Albert Instrument Company of Philadelphia, Pa. One hundred milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 centimeter diameter circle having an exposed area of approximately 33.17 square centimeters.

The pans are placed in a forced air oven at 100° F. (32° C.) for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows:

$$\text{Test MVTR} = (\text{grams weight loss over 24 hours}) \times 315.5 \text{ g/m}^2\text{-24 hours}$$

The relative humidity within the oven is not specifically controlled.

Under predetermined set conditions of 100° F. (32° C.) and ambient relative humidity, the MVTR for the CELGARD® 2500 control has been defined to be 5000 grams per square meter for 24 hours. Accordingly, the control sample is run with each test and the preliminary test values are corrected to set conditions using the following equation:

$$\text{MVTR} = (\text{Test MVTR/control MVTR}) \times (5000 \text{ g/m}^2\text{-24 hours})$$

While the embodiments disclosed herein are presently considered preferred, various modifications and improvements can be made without departing from the spirit and scope of the invention. The scope of the invention is indicated by the appended claims, and all changes that fall within the meaning and range of equivalency are intended to be embraced therein.

We claim:

1. An absorbent article, comprising:
   a liquid-permeable body-side liner;
   a non-absorbent surge material abutting the body-side liner;
   an outer cover of a substantially liquid-impermeable non-absorbent outer cover material abutting the surge material;
   a plurality of pockets in at least one of the surge material or the outer cover material; and
   a superabsorbent material in at least some of the pockets.

2. The absorbent article of claim 1, wherein the pockets are formed in the surge material.

3. The absorbent article of claim 1, wherein the pockets have depths of at least about 0.1 inch (2.5 mm), and diameters of about 0.2–1.0 inch (5–25 mm).

4. The absorbent article of claim 1, wherein the pockets have depths of about 0.15–0.50 inch (3.8–13 mm), and diameters of about 0.25–0.75 inch (6.4–19 mm).

5. The absorbent article of claim 1, wherein the pockets have depths of about 0.20–0.30 inch (5.1–7.6 mm), and diameters of about 0.40–0.60 inch (10–15 mm).

6. The absorbent article of claim 1, wherein the pockets are spaced apart at distances of about 0.05–1.5 inch (1.3–38 mm).

7. The absorbent article of claim 1, wherein the pockets are spaced apart at distances of about 0.10–1.0 inch (2.5–25 mm).

8. The absorbent article of claim 1, wherein the pockets are spaced apart at distances of about 0.15–0.50 inch (3.8–13 mm).

9. The absorbent article of claim 1, wherein each pocket comprises about 25–500 mg of the superabsorbent.

10. The absorbent article of claim 1, wherein each pocket comprises about 50–300 mg of the superabsorbent.

11. The absorbent article of claim 1, wherein each pocket comprises about 100–200 mg of the superabsorbent.

12. An absorbent article, comprising:
    a liquid permeable body-side liner;
    a surge material, formed of a non-absorbent material;
    a substantially liquid-impermeable outer cover, formed of a non-absorbent outer cover material;
    a plurality of pockets in at least one of the surge material and the outer cover material; and
    a superabsorbent material in at least some of the pockets;
    wherein the absorbent article is devoid of a separate absorbent layer between the surge material and the outer cover material.

13. The absorbent article of claim 12, wherein the pockets are formed in the surge material.

14. The absorbent article of claim 12, wherein the material in which the pockets are formed comprises a thermoplastic polymer.

15. The absorbent article of claim 12, wherein the material in which the pockets are formed comprises a thermoplastic nonwoven fibrous web.

16. The absorbent article of claim 15, wherein the nonwoven web comprises a neck-stretched nonwoven web.

17. The absorbent article of claim 13, wherein the surge material comprises a nonwoven fibrous web.

18. The absorbent article of claim 12, wherein the outer cover material comprises a nonwoven fibrous web and a breathable thermoplastic film.

19. An absorbent article, comprising:
    a non-absorbent surge material including at least one layer of a fibrous non-absorbent material;
    a non-absorbent outer cover material abutting the surge material and including at least one other layer of a fibrous non-absorbent material;
    a plurality of pockets in at least one of the surge material or the outer cover material; and
    a superabsorbent material in at least some of the pockets.

20. The absorbent article of claim 19, comprising a diaper.

21. The absorbent article of claim 19, comprising training pants.

22. The absorbent article of claim 19, comprising swim wear.

23. The absorbent article of claim 19, comprising absorbent underpants.

24. The absorbent article of claim 19, comprising a baby wipe.

25. The absorbent article of claim 19, comprising an adult incontinence product.

26. The absorbent article of claim 19, comprising a feminine hygiene product.

27. The absorbent article of claim 19, comprising a medical absorbent product.

* * * * *

UNITED STATES PATENT AND TRADEMARK OFFICE
CERTIFICATE OF CORRECTION

PATENT NO. : 6,429,350 B1
DATED : August 6, 2002
INVENTOR(S) : Richard Warren Tanzer et al.

It is certified that error appears in the above-identified patent and that said Letters Patent is hereby corrected as shown below:

<u>Title page, Item [54], and Column 1, lines 1-3,</u>
delete in their entirety and in its place insert:

-- ABSORBENT ARTICLE HAVING SUPERABSORBENT POCKETS IN A NON-ABSORBENT LAYER. --

Signed and Sealed this

Twenty-ninth Day of April, 2003

JAMES E. ROGAN
*Director of the United States Patent and Trademark Office*